US007438921B2

(12) United States Patent
First

(10) Patent No.: US 7,438,921 B2
(45) Date of Patent: *Oct. 21, 2008

(54) BUTTOCK DEFORMITY TREATMENT

(75) Inventor: Eric R. First, Boston, MA (US)

(73) Assignee: Allergan, Inc., Irvine, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 11/622,420

(22) Filed: Jan. 11, 2007

(65) Prior Publication Data

US 2007/0128228 A1 Jun. 7, 2007

Related U.S. Application Data

(63) Continuation of application No. 10/934,810, filed on Sep. 3, 2004, now Pat. No. 7,179,474.

(51) Int. Cl.
A61K 39/08 (2006.01)
A61K 39/02 (2006.01)

(52) U.S. Cl. .................. 424/239.1; 424/9.1; 424/236.1; 514/2; 514/12; 530/350; 530/412

(58) Field of Classification Search .............. 424/239.1, 424/9.1, 236.1; 514/12, 2; 530/350, 412
See application file for complete search history.

(56) References Cited

U.S. PATENT DOCUMENTS

| 5,298,019 | A | 3/1994 | Borodic | 604/51 |
|---|---|---|---|---|
| 5,437,291 | A | 8/1995 | Pasricha et al. | 128/898 |
| 5,670,484 | A | 9/1997 | Binder | 514/14 |
| 5,714,468 | A | 2/1998 | Binder | 514/14 |
| 5,766,605 | A | 6/1998 | Sanders et al. | 424/239.1 |
| 5,989,545 | A | 11/1999 | Foster et al. | 424/183.1 |
| 6,063,768 | A | 5/2000 | First | 514/14 |
| 6,113,915 | A | 9/2000 | Aoki et al. | 424/236.1 |
| 6,139,845 | A | 10/2000 | Donovan | 424/236.1 |
| 6,143,306 | A | 11/2000 | Donovan | 424/236.1 |
| 6,261,572 | B1 | 7/2001 | Donovan | 424/239.1 |
| 6,265,379 | B1 | 7/2001 | Donovan | 514/14 |
| 6,299,893 | B1 | 10/2001 | Schwartz et al. | 424/422 |
| 6,306,423 | B1 | 10/2001 | Donovan et al. | 424/423 |
| 6,312,708 | B1 | 11/2001 | Donovan | 424/423 |
| 6,365,164 | B1 | 4/2002 | Schmidt | 424/239.1 |
| 6,423,319 | B1 | 7/2002 | Brooks et al. | 424/239.1 |
| 6,447,787 | B1 | 9/2002 | Gassner et al. | 424/247.1 |
| 6,458,365 | B1 | 10/2002 | Aoki et al. | 424/239.1 |
| 6,464,986 | B1 | 10/2002 | Aoki et al. | 424/239.1 |
| 6,623,742 | B2 | 9/2003 | Voet | 424/236.1 |
| 6,667,041 | B2 | 12/2003 | Schmidt | 424/239.1 |
| 7,179,474 | B2 * | 2/2007 | First | 424/239.1 |
| 2003/0054975 | A1 | 3/2003 | Voet | 514/2 |
| 2003/0224019 | A1 | 12/2003 | O'Brien | 424/239.1 |
| 2004/0009180 | A1 | 1/2004 | Donovan | 424/184.1 |
| 2004/0213811 | A1 | 10/2004 | Ackerman | 424/239.1 |

FOREIGN PATENT DOCUMENTS

| WO | WO 95/05842 | 3/1995 |
|---|---|---|
| WO | WO 96/33273 | 4/1996 |
| WO | WO 98/07864 | 2/1998 |
| WO | WO 99/17806 | 4/1999 |
| WO | WO 00/10598 | 3/2000 |
| WO | WO 00/15245 | 3/2000 |
| WO | WO 00/57897 | 3/2000 |
| WO | WO 00/74703 | 5/2000 |
| WO | WO 01/21213 | 3/2001 |
| WO | WO 03/011333 | 2/2003 |

OTHER PUBLICATIONS

Aoki, K., et al, *Mechanisms of the antinociceptive effect of subcutaneous Botox: Inhibition of peripheral and central nociceptive processing*, Cephalalgia Sep. 2003;23(7):649.

Bigalke, H., et al., *Botulinum A Neurotoxin Inhibits Non-Cholinergic Synaptic Transmission in Mouse Spinal Cord Neurons in Culture*, Brain Research 360;318-324:1985.

Bigalke, H., et al., *Tetanus Toxin and Botulinum A Toxin Inhibit Release and Uptake of Various Transmitters, as Studied with Particulate Preparations From Rat Brain and Spinal Cord*, Naunyn-Schmiedeberg's Arch Pharmacol 316;244-251:1981.

Binz, T. et al., *The Complete Sequence of Botulinum Neurotoxin Type A and Comparison with Other Clostridial Neurotoxins*, J Biological Chemistry 265(16);9153-9158:1990.

Blugerman, G., et al., *Multiple eccrine hidrocystomas: A new therapeutic option with botulinum toxin*, Dermatol Surg May 2003;29(5):557-9.

Borodic et al., *Pharmacology and Histology fo the therapeutic Application of Botulinum Toxin*, Therapy With Botulinum Toxin, Ed. Jankovic, J., et al., Marcel Dekker, Inc., (1994), p. 150.

Boyd et al., Movement Disorders, vol. 10, No. 3 (1995), p. 376.

Brem, H., et al, *Placebo-Controlled Trial of Safety and Efficacy of Intraoperative Controlled Delivery by Biodegradable Polymers of Chemotherapy for Recurrent Gliomas*, Lancet 345;1008-1012:1995.

Bushara, K., *Botulinum toxin and rhinorrhea*, Otolaryngol Head Neck Surg 1996;114(3):507.

Childers et al., (2002), American Journal of Physical Medicine & Rehabilitation, 81:751-759.

Coffield et al., *Site and Action of Botulinum Neurotoxin*, Therapy With Botulinum Toxin, Ed. Jankovic, J., et al., Marcel Dekker, Inc., (1994), p. 5.

(Continued)

Primary Examiner—Chih-Min Kam
(74) Attorney, Agent, or Firm—Claude L. Nassif; Stephen Donovan; Martin Voet

(57) ABSTRACT

Methods for treating a buttock deformity or for preventing development of a buttock deformity by local administration of a Clostridial toxin, such as a *botulinum* neurotoxin, to a buttock deformity or to the vicinity of a buttock deformity.

9 Claims, No Drawings

OTHER PUBLICATIONS

Dabrowski, E., et al., *Botulinum toxin as a novel treatment for self mutilation in Lesch-Nyhan syndrome*, Ann Neurol Sep. 2002;52(3 Supp 1):S157.

Doggweiler, R., et al., *Botulinum toxin type A causes diffuse and highly selective atrophy of rat prostate*, Neurourol Urodyn 1998;17(4):363.

Fung, L. K. et al., *Pharmacokinetics of Interstitial Delivery of Carmustine 4-Hydroperoxycyclophosphamide and Paclitaxel From a Biodegradable Polymer Implant in the Monkey Brain*, Cancer Research 58; 672-684:1998.

Goldman, (2000), Aesthetic Plastic Surgery Jul.-Aug. 24(4):280-282.

Gonelle-Gispert, Carmen, et al., *SNAP-25a and -25b Isoforms are Both Expressed in Insulin-Secreting Cells and Can Function in Insulin Secretion*, Biochem J. (1999) 339 (pt 1); pp. 159-165.

Habermann, E., et al., *Tetanus Toxin and Botulinum A and C Neurotoxins Inhibit Noradrenaline Release From Cultured Mouse Brain*, J Neurochem 51(2);522-527:1988.

Habermann, E., *Inhibition by Tetanus and Botulinum A Toxin of the release of [3H]Noradrenaline and [3H]GABA From Rat Brain Homogenate*, Experientia 44;224-226:1988.

Habermann, E., *Naunyn-Schmiedeberg's Arch. Pharmacol.* 1974; 281, 47-56.

*Harrison's Principles of Internal Medicine* (1998), edited by Anthony Fauci et al., 14th edition, published by McGraw Hill.

Heckmann, M., et al., *Botulinum toxin type A injection in the treatment of lichen simplex: An open pilot study*, J Am Acad Dermatol Apr. 2002;46(4):617-9.

Jost, W., *Ten years' experience with botulinum toxin in anal fissure*, Int J Colorectal Dis Sep. 2002;17(5):298-302.

Katsambas, A., et al., *Cutaneous diseases of the foot: Unapproved treatments*, Clin Dermatol Nov.-Dec. 2002;20(6):689-699.

Li, Y., et al., *Sensory and motor denervation influences epidermal thickness in rat foot glabrous skin*, Exp Neurol 1997;147:452-462 (see p. 459).

Marchese-Ragona, R. et al., *Management of Parotid Sialocele With Botulinum Toxin*, The Laryngoscope 109 (Aug. 1999):1344-1346.

Ahn, Jeffrey, et al., *Botulinum toxin for masseter reduction in asian patients*, Arch Facial Plast Surg, vol. 6, May/Jun. 2004, pp. 188-191.

Childers, Martin K., et al., *Botulinum toxin use in piriformis muscle syndrome: a double-blind study*, Arch Phys Med Rehabil, 2000, 81(9):1289, Poster 142.

Fishman, L., *Myobloc in the treatment of piriformis syndrome: a dose-finding study*, Naunyn Schmiedebergs Arch Pharmacol, Jun. 2002, 365 (Suppl 2):R20.

Fishman, L., *Myobloc in the treatment of piriformis syndrome—a dose-finding study*, Pain Med, 2002, 3(2), pp. 182-183 (Abstract).

Lee, Hyun-Jeong, et al., *Botulinum toxin A for aesthetic contouring of enlarged medial gastrocnemius muscle*, Dermatol Surg, 2004, 30, pp. 867-871.

Moyer, E., et al., *Botulinum Toxin Type B: Experimental and Clinical Experience*, being chapter 6, pp. 71-85 of "Therapy With Botulinum Toxin," edited by Jankovic, J. et al. (1994), Marcel Dekker, Inc.

Naumann, Markus, et al., *Botulinum Toxin Type A in the Treatment of Focal, Axillary and Palmar Hyperhidrosis and Other Hyperhidrotic Conditions*, European J. Neurology 6 (Supp 4): S111-S1150:1999.

Pearce, L.B., *Pharmacologic Characterization of Botulinum Toxin For Basic Science and Medicine*, Toxicon 35(9);1373-1412 at 1393, 1997.

Rogers, J., et al., *Injections of botulinum toxin A in foot dystonia*, Neurology Apr. 1993;43(4 Suppl 2).

Sanchez-Prieto, J., et al., *Botulinum Toxin A Blocks Glutamate Exocytosis From Guinea Pig Cerebral Cortical Synaptosomes*, Eur J. Biochem 165;675-681:1987.

Schantz, E.J., et al., *Properties and use of Botulinum toxin and Other Microbial Neurotoxins in Medicine*, Microbiol Rev. 56;80-99:1992.

Senior, M., *Botox and the management of pectoral spasm after subpectoral implant insertion*, Plastic and Recon Surg, Jul. 2000, 224-225.

Sevim, S., et al., *Botulinum toxin-A therapy for palmar and plantar hyperhidrosis*, Acta Neurol Belg Dec. 2002;102(4):167-70.

Singh, *Critical Aspects of Bacterial Protein Toxins*, pp. 63-84 (chapter 4) of Natural Toxins II, edited by B.R. Singh et al., Plenum Press, New York (1976).

Sloop, R. et al., *Reconstituted botulinum toxin type A does not lose potency in humans if it is refrozen or refrigerated before 2 weeks before use*, Neurology 48 (Jan. 1997):249-53:1997.

Suputtitada, A., *Local botulinum toxin type A injections in the treatment of spastic toes*, Am J Phys Med Rehabil Oct. 2002;81(10):770-5.

Tacks, L., et al., *Idiopathic toe walking: Treatment with botulinum toxin A injection*, Dev Med Child Neurol 2002;44(Suppl 91):6.

Weigand, et al., *Naunyn-Schmiedeberg's Arch. Pharmacol.* 1976; 292, 161-165.

\* cited by examiner

BUTTOCK DEFORMITY TREATMENT

CROSS-REFERENCE

This application is a continuation of U.S. application Ser. No. 10/934,810, filed Sep. 3, 2004, now U.S. Pat. No. 7,179,474, the content of which is hereby incorporated by reference in its entirely.

BACKGROUND

The present invention relates to methods for treating a buttock deformity. In particular, the present invention relates to methods for treating a buttock deformity by administration of a Clostridial neurotoxin, such as a *botulinum* toxin, to a patient.

A buttock is a prominence formed in large part by the gluteal muscles. In the normal condition, human have two buttocks located dorsally above the thighs and below the back. There are three gluteal muscles, the gluteus maximus, gluteus medius and gluteus minimus muscles. The bulk of a buttock is formed by the gluteus maximus muscle. The gluteus maximus originates from the ilium behind the posterior gluteal line on the posterior surface of the sacrum and coccyx and inserts into the iliotibial band and the gluteal tuberosity of the femur. The gluteus maximus allows for the extension of the thigh, especially from the flexed position, as in climbing stairs or rising from a sitting position. The gluteus medius is partly covered by the gluteus maximus. The gluteus medius originates from the ilium between the anterior and posterior gluteal lines and inserts into the lateral surface of the greater trochanter. The gluteus medius allows for the abduction and rotation of the thigh. The gluteus minimus lies beneath the gluteus medius. The gluteus minimus originates from the ilium between the anterior and inferior gluteal lines and inserts into the greater trochanter of the femur and it facilitates the gluteus medius in the abduction of the thigh. In the normal buttock, the glutei musculature forms well rounded and symmetrical buttocks with a horizontal gluteal line.

A buttock deformity can include a large or prominent buttock, a deficient or flat buttock, lack of or an uneven buttock crease and fold, a depression in a buttock, a square shaped buttock, an irregularly shaped or asymmetric buttock or ptosis (sagging) of a buttock. A buttock deformity can be the result of a birth defect, injury, surgery (including prior cosmetic surgery) or of a perceived or actual cosmetic deficiency or defect.

Flattening of the upper, outer quadrant of the buttock or a loosely hanging appearance of the buttock suggests weakness of the gluteus maximus or inhibition of the muscle due to tightness of the hip flexors or sacroiliac joint dysfunction. In the case of sacroiliac joint dysfunction changes in muscle activation can occur due to arthrogenic inhibition of the gluteus maximus on the side of the blocked joint and of the gluteus medius on the contralateral side. Painful spasms of the iliacus, piriformis and rectos abdominis can also occur.

An injury which results in a buttock defect can begin as a hematoma (as can result from a fall) which reduces fat levels within the buttock form. Upon drainage or resorbtion of the hematoma a depression can remain. Surgery can result in a buttock contour irregularity. Additionally steroid injections into a fatty portion of a buttock can cause absorption and atrophy of fat cells, which can result a buttock depression. A buttock deformity can be due to surgery for example from use of abdominal liposuction which removes buttock supporting tissue and can causes ptosis (drooping or sagging) of a buttock.

Cosmetic surgery to a buttock can be for a variety of reasons, such as to alter and thereby enhance a buttock shape (as by use of buttock implants or by using liposuction to create a different buttock fold and contour), to reduce a buttock prominence (as through liposuction). Patients can seek liposuction of the buttocks to create a better fold and contour.

Limb length discrepancy is a condition where one leg is longer than the other. When a substantial difference exist disruptive effects on gait and posture can occur. For a functional limb length discrepancy, related to abnormal pronation of the foot, a functional orthotic device to correct the pronatory motion may be sufficient. Muscle strengthening and stretching is also an important part of the functional deformity therapy. For a combination of functional and structural deformity, a combination of lifts and orthotics may be required. Purely structural deformities can require lifts.

*Botulinum* Toxin

The genus *Clostridium* has more than one hundred and twenty seven species, grouped according to their morphology and functions. The anaerobic, gram positive bacterium *Clostridium botulinum* produces a potent polypeptide neurotoxin, *botulinum* toxin, which causes a neuroparalytic illness in humans and animals referred to as botulism. The spores of *Clostridium botulinum* are found in soil and can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The *botulinum* toxin can apparently pass unattenuated through the lining of the gut and shows a high affinity for cholinergic motor neurons. Symptoms of *botulinum* toxin intoxication can progress from difficulty walking, swallowing, and speaking to paralysis of the respiratory muscles and death.

*Botulinum* toxin type A is the most lethal natural biological agent known to man. About 50 picograms of a commercially available *botulinum* toxin type A (purified neurotoxin complex)[1] is a LD50 in mice (i.e. 1 unit). One unit of BOTOX® contains about 50 picograms (about 56 attomoles) of *botulinum* toxin type A complex. Interestingly, on a molar basis, *botulinum* toxin type A is about 1.8 billion times more lethal than diphtheria, about 600 million times more lethal than sodium cyanide, about 30 million times more lethal than cobra toxin and about 12 million times more lethal than cholera. Singh, *Critical Aspects of Bacterial Protein Toxins*, pages 63-84 (chapter 4) of Natural Toxins II, edited by B. R. Singh et al., Plenum Press, New York (1976) (where the stated LD50 of *botulinum* toxin type A of 0.3 ng equals 1 U is corrected for the fact that about 0.05 ng of BOTOX® equals 1 unit). One unit (U) of *botulinum* toxin is defined as the LD50 upon intraperitoneal injection into female Swiss Webster mice weighing 18 to 20 grams each.

[1] Available from Allergan, Inc., of Irvine, Calif. under the tradename BOTOX® in 100 unit vials)

Seven generally immunologically distinct *botulinum* neurotoxins have been characterized these being respectively *botulinum* neurotoxin serotypes A, B, $C_1$, D, E, F and G each of which is distinguished by neutralization with type-specific antibodies. The different serotypes of *botulinum* toxin vary in the animal species that they affect and in the severity and duration of the paralysis they evoke. For example, it has been determined that *botulinum* toxin type A is 500 times more potent, as measured by the rate of paralysis produced in the rat, than is *botulinum* toxin type B. Additionally, *botulinum* toxin type B has been determined to be non-toxic in primates at a dose of 480 U/kg which is about 12 times the primate LD50 for *botulinum* toxin type A. Moyer E et al., *Botulinum*-

Toxin Type B: *Experimental and Clinical Experience*, being chapter 6, pages 71-85 of "Therapy With *Botulinum* Toxin," edited by Jankovic, J. et al. (1994), Marcel Dekker, Inc. *Botulinum* toxin apparently binds with high affinity to cholinergic motor neurons, is translocated into the neuron and blocks the release of acetylcholine. Additional uptake can take place through low affinity receptors, as well as by phagocytosis and pinocytosis.

Regardless of serotype, the molecular mechanism of toxin intoxication appears to be similar and to involve at least three steps or stages. In the first step of the process, the toxin binds to the presynaptic membrane of the target neuron through a specific interaction between the heavy chain (the H chain or HC), and a cell surface receptor. The receptor is thought to be different for each type of *botulinum* toxin and for tetanus toxin. The carboxyl end segment of the HC appears to be important for targeting of the *botulinum* toxin to the cell surface.

In the second step, the *botulinum* toxin crosses the plasma membrane of the target cell. The *botulinum* toxin is first engulfed by the cell through receptor-mediated endocytosis, and an endosome containing the *botulinum* toxin is formed. The toxin then escapes the endosome into the cytoplasm of the cell. This step is thought to be mediated by the amino end segment of the HC, the HN, which triggers a conformational change of the toxin in response to a pH of about 5.5 or lower. Endosomes are known to possess a proton pump which decreases intra-endosomal pH. The conformational shift exposes hydrophobic residues in the toxin, which permits the *botulinum* toxin to embed itself in the endosomal membrane. The *botulinum* toxin (or at least the light chain of the *botulinum*) then translocates through the endosomal membrane into the cytoplasm.

The last step of the mechanism of *botulinum* toxin activity appears to involve reduction of the disulfide bond joining the heavy chain, H chain, and the light chain, L chain. The entire toxic activity of *botulinum* and tetanus toxins is contained in the L chain of the holotoxin; the L chain is a zinc (Zn++) endopeptidase which selectively cleaves proteins essential for recognition and docking of neurotransmitter-containing vesicles with the cytoplasmic surface of the plasma membrane, and fusion of the vesicles with the plasma membrane. Tetanus neurotoxin, *botulinum* toxin types B, D, F, and G cause degradation of synaptobrevin (also called vesicle-associated membrane protein (VAMP)), a synaptosomal membrane protein. Most of the VAMP present at the cytoplasmic surface of the synaptic vesicle is removed as a result of any one of these cleavage events. *Botulinum* toxin serotype A and E cleave SNAP-25. *Botulinum* toxin serotype C1 was originally thought to cleave syntaxin, but was found to cleave syntaxin and SNAP-25. Each of the *botulinum* toxins specifically cleaves a different bond, except *botulinum* toxin type B (and tetanus toxin) which cleave the same bond. Each of these cleavages block the process of vesicle-membrane docking, thereby preventing exocytosis of vesicle content.

*Botulinum* toxins have been used in clinical settings for the treatment of neuromuscular disorders characterized by hyperactive skeletal muscles (i.e. motor disorders). In 1989, a *botulinum* toxin type A complex was approved by the U.S. Food and Drug Administration for the treatment of blepharospasm, strabismus and hemifacial spasm. Subsequently, a *botulinum* toxin type A was also approved by the FDA for the treatment of cervical dystonia and for the treatment of glabellar lines, and a *botulinum* toxin type B was approved for the treatment of cervical dystonia. Non-type A *botulinum* toxin serotypes apparently have a lower potency and/or a shorter duration of activity as compared to *botulinum* toxin type A. Clinical effects of peripheral intramuscular *botulinum* toxin type A are usually seen within one week of injection. The typical duration of symptomatic relief from a single intramuscular injection of *botulinum* toxin type A averages about three months, although significantly longer periods of therapeutic activity have been reported.

Although all the *botulinum* toxins serotypes apparently inhibit release of the neurotransmitter acetylcholine at the neuromuscular junction, they do so by affecting different neurosecretory proteins and/or cleaving these proteins at different sites. For example, *botulinum* types A and E both cleave the 25 kiloDalton (kD) synaptosomal associated protein (SNAP-25), but they target different amino acid sequences within this protein. *Botulinum* toxin types B, D, F and G act on vesicle-associated protein (VAMP, also called synaptobrevin), with each serotype cleaving the protein at a different site. Finally, *botulinum* toxin type C1 has been shown to cleave both syntaxin and SNAP-25. These differences in mechanism of action may affect the relative potency and/or duration of action of the various *botulinum* toxin serotypes. Apparently, a substrate for a *botulinum* toxin can be found in a variety of different cell types. See e.g. *Biochem J* 1;339 (pt 1):159-65:1999, and *Mov Disord*, 10(3):376:1995 (pancreatic islet B cells contains at least SNAP-25 and synaptobrevin).

The molecular weight of the *botulinum* toxin protein molecule, for all seven of the known *botulinum* toxin serotypes, is about 150 kD. Interestingly, the *botulinum* toxins are released by Clostridial bacterium as complexes comprising the 150 kD *botulinum* toxin protein molecule along with associated non-toxin proteins. Thus, the *botulinum* toxin type A complex can be produced by Clostridial bacterium as 900 kD, 500 kD and 300 kD forms. *Botulinum* toxin types B and C1 are apparently produced as only a 700 kD or 500 kD complex. *Botulinum* toxin type D is produced as both 300 kD and 500 kD complexes. Finally, *botulinum* toxin types E and F are produced as only approximately 300 kD complexes. The complexes (i.e. molecular weight greater than about 150 kD) are believed to contain a non-toxin hemagglutinin proteins and a non-toxin and non-toxic nonhemagglutinin protein. These two non-toxin proteins (which along with the *botulinum* toxin molecule comprise the relevant neurotoxin complex) may act to provide stability against denaturation to the *botulinum* toxin molecule and protection against digestive acids when a *botulinum* toxin is ingested. Additionally, it is possible that the larger (greater than about 150 kD molecular weight) *botulinum* toxin complexes may result in a slower rate of diffusion of the *botulinum* toxin away from a site of intramuscular injection of a *botulinum* toxin complex.

In vitro studies have indicated that *botulinum* toxin inhibits potassium cation induced release of both acetylcholine and norepinephrine from primary cell cultures of brainstem tissue. Additionally, it has been reported that *botulinum* toxin inhibits the evoked release of both glycine and glutamate in primary cultures of spinal cord neurons and that in brain synaptosome preparations *botulinum* toxin inhibits the release of each of the neurotransmitters acetylcholine, dopamine, norepinephrine (Habermann E., et al., *Tetanus Toxin and Botulinum A and C Neurotoxins Inhibit Noradrenaline Release From Cultured Mouse Brain*, J Neurochem 51(2);522-527:1988) CGRP, substance P and glutamate (Sanchez-Prieto, J., et al., *Botulinum Toxin A Blocks Glutamate Exocytosis From Guinea Pig Cerebral Cortical Synaptosomes*, Eur J. Biochem 165;675-681:1897. Thus, when adequate concentrations are used, stimulus-evoked release of most neurotransmitters can be blocked by *botulinum* toxin. See e.g. Pearce, L. B., *Pharmacologic Character-* ization of Botulinum Toxin For Basic Science and Medicine, Toxicon 35(9);1373-1412 at 1393; Bigalke H., et al., Botulinum A Neurotoxin Inhibits Non-Cholinergic Synaptic Transmission in Mouse Spinal Cord Neurons in Culture, Brain Research 360;318-324:1985; Habermann E., Inhibition by Tetanus and Botulinum A Toxin of the release of [3H]Noradrenaline and [3H]GABA From Rat Brain Homogenate, Experientia 44;224-226:1988, Bigalke H., et al., Tetanus Toxin and Botulinum A Toxin Inhibit Release and Uptake of Various Transmitters, as Studied with Particulate Preparations From Rat Brain and Spinal Cord, Naunyn-Schmiedeberg's Arch Pharmacol 316;244-251:1981, and; Jankovic J. et al., Therapy With Botulinum Toxin, Marcel Dekker, Inc., (1994), page 5.

Botulinum toxin type A can be obtained by establishing and growing cultures of Clostridium botulinum in a fermenter and then harvesting and purifying the fermented mixture in accordance with known procedures. All the botulinum toxin serotypes are initially synthesized as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes C1, D and E are synthesized by non-proteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture. Therefore, a certain percentage of any preparation of, for example, the botulinum toxin type B toxin is likely to be inactive, possibly accounting for the known significantly lower potency of botulinum toxin type B as compared to botulinum toxin type A. The presence of inactive botulinum toxin molecules in a clinical preparation will contribute to the overall protein load of the preparation, which has been linked to increased antigenicity, without contributing to its clinical efficacy. Additionally, it is known that botulinum toxin type B has, upon intramuscular injection, a shorter duration of activity and is also less potent than botulinum toxin type A at the same dose level.

High quality crystalline botulinum toxin type A can be produced from the Hall A strain of Clostridium botulinum with characteristics of $\geq 3 \times 10^7$ U/mg, an A260/A278 of less than 0.60 and a distinct pattern of banding on gel electrophoresis. The known Shantz process can be used to obtain crystalline botulinum toxin type A, as set forth in Shantz, E. J., et al, Properties and use of Botulinum toxin and Other Microbial Neurotoxins in Medicine, Microbiol Rev. 56;80-99:1992. Generally, the botulinum toxin type A complex can be isolated and purified from an anaerobic fermentation by cultivating Clostridium botulinum type A in a suitable medium. The known process can also be used, upon separation out of the non-toxin proteins, to obtain pure botulinum toxins, such as for example: purified botulinum toxin type A with an approximately 150 kD molecular weight with a specific potency of $1-2 \times 10^8$ LD50 U/mg or greater; purified botulinum toxin type B with an approximately 156 kD molecular weight with a specific potency of $1-2 \times 10^8$ LD50 U/mg or greater, and; purified botulinum toxin type F with an approximately 155 kD molecular weight with a specific potency of $1-2 \times 10^7$ LD50 U/mg or greater.

Botulinum toxins and/or botulinum toxin complexes can be obtained from List Biological Laboratories, Inc., Campbell, Calif.; the Centre for Applied Microbiology and Research, Porton Down, U.K.; Wako (Osaka, Japan), Metabiologics (Madison, Wis.) as well as from Sigma Chemicals of St Louis, Mo. Pure botulinum toxin can also be used to prepare a pharmaceutical composition.

As with enzymes generally, the biological activities of the botulinum toxins (which are intracellular peptidases) are dependant, at least in part, upon their three dimensional conformation. Thus, botulinum toxin type A is detoxified by heat, various chemicals surface stretching and surface drying. Additionally, it is known that dilution of a botulinum toxin complex obtained by the known culturing, fermentation and purification to the much, much lower toxin concentrations used for pharmaceutical composition formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Since the botulinum toxin may be used months or years after the toxin containing pharmaceutical composition is formulated, the toxin can be stabilized with a stabilizing agent such as albumin and gelatin.

A commercially available botulinum toxin containing pharmaceutical composition is sold under the trademark BOTOX® (available from Allergan, Inc., of Irvine, Calif.). BOTOX® consists of a purified botulinum toxin type A complex, albumin and sodium chloride packaged in sterile, vacuum-dried form. The botulinum toxin type A is made from a culture of the Hall strain of Clostridium botulinum grown in a medium containing N-Z amine and yeast extract. The botulinum toxin type A complex is purified from the culture solution by a series of acid precipitations to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. The vacuum-dried product is stored in a freezer at or below −5° C. BOTOX® can be reconstituted with sterile, non-preserved saline prior to intramuscular injection. Each vial of BOTOX® contains about 100 units (U) of Clostridium botulinum toxin type A purified neurotoxin complex, 0.5 milligrams of human serum albumin and 0.9 milligrams of sodium chloride in a sterile, vacuum-dried form without a preservative.

To reconstitute vacuum-dried BOTOX®, sterile normal saline without a preservative; (0.9% Sodium Chloride Injection) is used by drawing up the proper amount of diluent in the appropriate size syringe. Since BOTOX® may be denatured by bubbling or similar violent agitation, the diluent is gently injected into the vial. For sterility reasons BOTOX® is preferably administered within four hours after the vial is removed from the freezer and reconstituted. During these four hours, reconstituted BOTOX® can be stored in a refrigerator at about 2° C. to about 8° C. Reconstituted, refrigerated BOTOX® has been reported to retain its potency for at least about two weeks. Neurology, 48:249-53:1997.

It has been reported that botulinum toxin type A has been used in clinical settings as follows:
(1) about 75-125 units of BOTOX® per intramuscular injection (multiple muscles) to treat cervical dystonia;
(2) 5-10 units of BOTOX® per intramuscular injection to treat glabellar lines (brow furrows) (5 units injected intramuscularly into the procerus muscle and 10 units injected intramuscularly into each corrugator supercilli muscle);

(3) about 30-80 units of BOTOX® to treat constipation by intrasphincter injection of the puborectalis muscle;

(4) about 1-5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.

(5) to treat strabismus, extraocular muscles have been injected intramuscularly with between about 1-5 units of BOTOX®, the amount injected varying based upon both the size of the muscle to be injected and the extent of muscle paralysis desired (i.e. amount of diopter correction desired).

(6) to treat upper limb spasticity following stroke by intramuscular injections of BOTOX® into five different upper limb flexor muscles, as follows:

(a) flexor digitorum profundus: 7.5 U to 30 U
(b) flexor digitorum sublimus: 7.5 U to 30 U
(c) flexor carpi ulnaris: 10 U to 40 U
(d) flexor carpi radialis: 15 U to 60 U
(e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.

(7) to treat migraine, pericranial injected (injected symmetrically into glabellar, frontalis and temporalis muscles) injection of 25 U of BOTOX® has showed significant benefit as a prophylactic treatment of migraine compared to vehicle as measured by decreased measures of migraine frequency, maximal severity, associated vomiting and acute medication use over the three month period following the 25 U injection.

It is known that *botulinum* toxin type A can have an efficacy for up to 12 months (*European J. Neurology* 6 (Supp 4): S111-S1150:1999), and in some circumstances for as long as 27 months, when used to treat glands, such as in the treatment of hyperhydrosis. See e.g. Bushara K., *Botulinum toxin and rhinorrhea,* Otolaryngol Head Neck Surg 1996;114(3):507, and *The Laryngoscope* 109:1344-1346:1999. However, the usual duration of an intramuscular injection of Botox® is typically about 3 to 4 months.

The success of *botulinum* toxin type A to treat a variety of clinical conditions has led to interest in other *botulinum* toxin serotypes. Two commercially available *botulinum* type A preparations for use in humans are BOTOX® available from Allergan, Inc., of Irvine, Calif., and Dysport® available from Beaufour Ipsen, Porton Down, England. A *Botulinum* toxin type B preparation (MyoBloc®) is available from Elan Pharmaceuticals of San Francisco, Calif.

In addition to having pharmacologic actions at the peripheral location, *botulinum* toxins may also have inhibitory effects in the central nervous system. Work by Weigand et al, *Naunyn-Schmiedeberg's Arch. Pharmacol.* 1976; 292, 161-165, and Habermann, *Naunyn-Schmiedeberg's Arch. Pharmacol.* 1974; 281, 47-56 showed that *botulinum* toxin is able to ascend to the spinal area by retrograde transport. As such, a *botulinum* toxin injected at a peripheral location, for example intramuscularly, may be retrograde transported to the spinal cord.

A *botulinum* toxin has also been proposed for or has been used to treat skin bone and tendon wounds (U.S. Pat. No. 6,447,787); intrathecal pain (see e.g. U.S. Pat. No. 6,113,915); various autonomic nerve disorders, including sweat gland disorders (see e.g. U.S. Pat. No. 5,766,605 and Goldman (2000), Aesthetic Plastic Surgery July-August 24(4): 280-282); tension headache (U.S. Pat. No. 6,458,365); migraine headache pain (U.S. Pat. No. 5,714,468); post-operative pain and visceral pain (U.S. Pat. No. 6,464,986); hair growth and hair retention (U.S. Pat. No. 6,299,893); psoriasis and dermatitis (U.S. Pat. No. 5,670,484); injured muscles (U.S. Pat. No. 6,423,319); various cancers (see e.g. U.S. Pat. Nos. 6,139,845 and 6,063,768), smooth muscle disorders (U.S. Pat. No. 5,437,291); nerve entrapment syndromes (U.S. patent application 2003 0224019); acne (WO 03/011333); neurogenic inflammation (U.S. Pat. No. 6,063,768); otic disorders (see e.g. U.S. Pat. No. 6,265,379); pancreatic disorders (see e.g. U.S. Pat. Nos. 6,143,306 and 6,261,572); prostate disorders, including prostatic hyperplasia, prostate cancer and urinary incontinence (see e.g. U.S. Pat. Nos. 6,365,164 and 6,667,041 and Doggweiler R., et al *Botulinum toxin type A causes diffuse and highly selective atrophy of rat prostate,* Neurourol Urodyn 1998;17(4):363); fibromyalgia (U.S. Pat. No. 6,623,742), and piriformis muscle syndrome (see e.g. Childers et al. (2002), American Journal of Physical Medicine & Rehabilitation, 81:751-759).

U.S. Pat. No. 5,989,545 discloses that a modified clostridial neurotoxin or fragment thereof, preferably a *botulinum* toxin, chemically conjugated or recombinantly fused to a particular targeting moiety can be used to treat pain by administration of the agent to the spinal cord. Additionally it has been disclosed that targeted *botulinum* toxins (i.e. with a non-native binding moiety) can be used to treat various conditions (see e.g. WO 96/33273; WO 99/17806; WO 98/07864; WO 00/57897; WO 01/21213; WO 00/10598.

A *botulinum* toxin has been injected into the pectoral muscle to control pectoral spasm. See e.g. Senior M., *Botox and the management of pectoral spasm after subpectoral implant insertion,* Plastic and Recon Surg, July 2000, 224-225. Controlled release toxin implants are known (see e.g. U.S. Pat. Nos. 6,306,423 and 6,312,708) as is transdermal *botulinum* toxin administration (U.S. patent application Ser. No. 10/194,805).

Both liquid stable formulations and pure *botulinum* toxin formulations have been disclosed (see e.g. WO 00/15245 and WO 74703) as well as topical application of a *botulinum* toxin (see e.g. DE 198 52 981).

It is known that a *botulinum* toxin can be used to: weaken the chewing or biting muscle of the mouth so that self inflicted wounds and resulting ulcers can heal (Payne M., et al, *Botulinum toxin as a novel treatment for self mutilation in Lesch-Nyhan syndrome,* Ann Neurol 2002 September; 52(3 Supp 1):S157); permit healing of benign cystic lesions or tumors (Blugerman G., et al., *Multiple eccrine hidrocystomas: A new therapeutic option with botulinum toxin,* Dermatol Surg 2003 May; 29(5):557-9); treat anal fissure (Jost W., *Ten years' experience with botulinum toxin in anal fissure,* Int J Colorectal Dis 2002 September; 17(5):298-302, and; treat certain types of atopic dermatitis (Heckmann M., et al., *Botulinum toxin type A injection in the treatment of lichen simplex: An open pilot study,* J Am Acad Dermatol 2002 April; 46(4):617-9).

Additionally, a *botulinum* toxin may have an effect to reduce induced inflammatory pain in a rat formalin model. Aoki K., et al, *Mechanisms of the antinociceptive effect of subcutaneous Botox: Inhibition of peripheral and central nociceptive processing,* Cephalalgia 2003 September; 23(7): 649. Furthermore, it has been reported that *botulinum* toxin nerve blockage can cause a reduction of epidermal thickness. Li Y, et al., *Sensory and motor denervation influences epidermal thickness in rat foot glabrous skin,* Exp Neurol 1997;147: 452-462 (see page 459). Finally, it is known to administer a *botulinum* toxin to the foot to treat excessive foot sweating (Katsambas A., et al., *Cutaneous diseases of the foot: Unapproved treatments,* Clin Dermatol 2002 November-December; 20(6):689-699; Sevim, S., et al., *Botulinum toxin-A therapy for palmar and plantar hyperhidrosis*, Acta Neurol Berg 2002 December; 102(4):167-70), spastic toes (Suputtitada, A., *Local botulinum toxin type A injections in the treatment of spastic toes*, Am J Phys Med Rehabil 2002 October; 81(10):770-5), idiopathic toe walking (Tacks, L., et al., *Idiopathic toe walking: Treatment with botulinum toxin A injection*, Dev Med Child Neurol 2002;44(Suppl 91):6), and foot dystonia (Rogers J., et al., *Injections of botulinum toxin A in foot dystonia*, Neurology 1993 April; 43(4 Suppl 2)).

Tetanus toxin, as wells as derivatives (i.e. with a non-native targeting moiety), fragments, hybrids and chimeras thereof can also have therapeutic utility. The tetanus toxin bears many similarities to the *botulinum* toxins. Thus, both the tetanus toxin and the *botulinum* toxins are polypeptides made by closely related species of *Clostridium* (*Clostridium tetani* and *Clostridium botulinum*, respectively). Additionally, both the tetanus toxin and the *botulinum* toxins are dichain proteins composed of a light chain (molecular weight about 50 kD) covalently bound by a single disulfide bond to a heavy chain (molecular weight about 100 kD). Hence, the molecular weight of tetanus toxin and of each of the seven *botulinum* toxins (non-complexed) is about 150 kD. Furthermore, for both the tetanus toxin and the *botulinum* toxins, the light chain bears the domain which exhibits intracellular biological (protease) activity, while the heavy chain comprises the receptor binding (immunogenic) and cell membrane translocational domains.

Further, both the tetanus toxin and the *botulinum* toxins exhibit a high, specific affinity for gangliocide receptors on the surface of presynaptic cholinergic neurons. Receptor mediated endocytosis of tetanus toxin by peripheral cholinergic neurons results in retrograde axonal transport, blocking of the release of inhibitory neurotransmitters from central synapses and a spastic paralysis. Contrarily, receptor mediated endocytosis of *botulinum* toxin by peripheral cholinergic neurons results in little if any retrograde transport, inhibition of acetylcholine exocytosis from the intoxicated peripheral motor neurons and a flaccid paralysis.

Finally, the tetanus toxin and the *botulinum* toxins resemble each other in both biosynthesis and molecular architecture. Thus, there is an overall 34% identity between the protein sequences of tetanus toxin and *botulinum* toxin type A, and a sequence identity as high as 62% for some functional domains. Binz T. et al., *The Complete Sequence of Botulinum Neurotoxin Type A and Comparison with Other Clostridial Neurotoxins*, J Biological Chemistry 265(16);9153-9158: 1990.

Acetylcholine

Typically only a single type of small molecule neurotransmitter is released by each type of neuron in the mammalian nervous system, although there is evidence which suggests that several neuromodulators can be released by the same neuron. The neurotransmitter acetylcholine is secreted by neurons in many areas of the brain, but specifically by the large pyramidal cells of the motor cortex, by several different neurons in the basal ganglia, by the motor neurons that innervate the skeletal muscles, by the preganglionic neurons of the autonomic nervous system (both sympathetic and parasympathetic), by the bag 1 fibers of the muscle spindle fiber, by the postganglionic neurons of the parasympathetic nervous system, and by some of the postganglionic neurons of the sympathetic nervous system. Essentially, only the postganglionic sympathetic nerve fibers to the sweat glands, the piloerector muscles and a few blood vessels are cholinergic as most of the postganglionic neurons of the sympathetic nervous system secret the neurotransmitter norepinephine. In most instances acetylcholine has an excitatory effect. However, acetylcholine is known to have inhibitory effects at some of the peripheral parasympathetic nerve endings, such as inhibition of heart rate by the vagal nerve.

The efferent signals of the autonomic nervous system are transmitted to the body through either the sympathetic nervous system or the parasympathetic nervous system. The preganglionic neurons of the sympathetic nervous system extend from preganglionic sympathetic neuron cell bodies located in the intermediolateral horn of the spinal cord. The preganglionic sympathetic nerve fibers, extending from the cell body, synapse with postganglionic neurons located in either a paravertebral sympathetic ganglion or in a prevertebral ganglion. Since, the preganglionic neurons of both the sympathetic and parasympathetic nervous system are cholinergic, application of acetylcholine to the ganglia will excite both sympathetic and parasympathetic postganglionic neurons.

Acetylcholine activates two types of receptors, muscarinic and nicotinic receptors. The muscarinic receptors are found in all effector cells stimulated by the postganglionic, neurons of the parasympathetic nervous system as well as in those stimulated by the postganglionic cholinergic neurons of the sympathetic nervous system. The nicotinic receptors are found in the adrenal medulla, as well as within the autonomic ganglia, that is on the cell surface of the postganglionic neuron at the synapse between the preganglionic and postganglionic neurons of both the sympathetic and parasympathetic systems. Nicotinic receptors are also found in many nonautonomic nerve endings, for example in the membranes of skeletal muscle fibers at the neuromuscular junction.

Acetylcholine is released from cholinergic neurons when small, clear, intracellular vesicles fuse with the presynaptic neuronal cell membrane. A wide variety of non-neuronal secretory cells, such as, adrenal medulla (as well as the PC12 cell line) and pancreatic islet cells release catecholamines and parathyroid hormone, respectively, from large dense-core vesicles. The PC12 cell line is a clone of rat pheochromocytoma cells extensively used as a tissue culture model for studies of sympathoadrenal development. *Botulinum* toxin inhibits the release of both types of compounds from both types of cells in vitro, permeabilized (as by electroporation) or by direct injection of the toxin into the denervated cell. *Botulinum* toxin is also known to block release of the neurotransmitter glutamate from cortical synaptosomes cell cultures.

A neuromuscular junction is formed in skeletal muscle by the proximity of axons to muscle cells. A signal transmitted through the nervous system results in an action potential at the terminal axon, with activation of ion channels and resulting release of the neurotransmitter acetylcholine from intraneuronal synaptic vesicles, for example at the motor endplate of the neuromuscular junction. The acetylcholine crosses the extracellular space to bind with acetylcholine receptor proteins on the surface of the muscle end plate. Once sufficient binding has occurred, an action potential of the muscle cell causes specific membrane ion channel changes, resulting in muscle cell contraction. The acetylcholine is then released from the muscle cells and metabolized by cholinesterases in the extracellular space. The metabolites are recycled back into the terminal axon for reprocessing into further acetylcholine.

What is needed therefore is a non-surgical method for effectively treating a buttock deformity.

SUMMARY

The present invention meets this need and provides methods for effectively treating a buttock deformity by local administration of a Clostridial neurotoxin, such as a *botulinum* toxin.

The following definitions apply herein:

"About" means approximately or nearly and in the context of a numerical value or range set forth herein means ±10% of the numerical value or range recited or claimed.

"Asymmetric ptosis of the buttock" means a buttock which sag or droops such that it has a decreased symmetry with regard to the other buttock.

"*Botulinum* toxin" means a *botulinum* neurotoxin (i.e. the *botulinum* neurotoxins types A, B, C, D, E, F and G) as either pure toxin (i.e. about 150 kDa weight molecule) or as a complex (i.e. about 300 to about 900 kDa weight complex comprising the neurotoxin molecule and one or more associated non-toxic molecules), and excludes *botulinum* toxins which are not neurotoxins such as the cytotoxic *botulinum* toxins C2 and C3, but includes recombinantly made, hybrid, modified, and chimeric *botulinum* neuro toxins.

"Buttock" means the gluteus maximus, gluteus medius, and/or gluteus minimus muscles, and the structures and tissues directly attendant to these muscles such as associated joints, tendons, ligaments, adipose tissues and overlying dermis.

"Buttock modification exercise" means an exercise carried out to stretch and/or strengthen a buttock muscle or attendant structure.

"Contour deformity" means a buttock with an undesirable shape or appearance.

"Deficient buttock" means a buttock that is at least 10% smaller than the average length, width and/or prominence of a buttock of persons of the same or similar size and weight as the patient.

"Deformity" means a cosmetic, physical or functional irregularity, defect, abnormality, imperfection, malformation or distortion. A "buttock deformity" excludes any buttock glandular deformity or defect, such as that of a secreting (including an excessively secreting) buttock sweat gland, because treatment of a buttock glandular defect is excluded from the scope of the present invention as treatment of a buttock gland can be difficult, painful, time consuming and therapeutically unsatisfactory to the patient and/or to the treating physician due to the sensitive nature of buttock tissues and the dispersed distribution of buttock glands, including buttock sweat glands. Moreover, treating buttock region sweat glands (to reduce the sweating) can have deleterious side effects. For example, in buttock deformity treatments where stretching and strengthening exercises are employed, sweating would be a desirable consequence to prevent overheating caused by the stretching and strengthening exercises. Also, treatment of a buttock deformity according to the present invention excludes administration of a *botulinum* toxin to a piriformis muscle because the piriformis muscle is a deep muscle that is not involved in buttock shaping or reshaping or in the ambulatory process. In addition, treatment to a piriformis muscle can cause unnecessary pain and unwanted functional side effects such as an inability to rotate or abduct a thigh. Furthermore, treatment of a buttock deformity excludes treatment of pain associated with the buttock because pain is a sensory perception and not a motor function involved in movement or providing structural support. Moreover, in treatment of buttock deformity where stretching and strengthening exercises are involved, pain is a necessary and a desired sensory perception to be retained so as to prevent or to signal overexertion and over-stretching.

"Depression in the buttock" means that the shape of the overall buttock is interrupted by a concavity in a portion of the buttock.

"Flat buttock" means one where there is a decreased overall curvature of the outline of the buttock (from a profile view) compared to the average buttock of other persons of the same or similar size and weight.

"Foot supporting device" means any device, such an orthotic or lift, used to improve gait or posture or to reduce pain caused by deformities in the back, hip, and/or lower extremities.

"Irregularly shaped buttock" means a buttock that deviates from the average shape of a buttock of persons of the same or similar size and weight as the patient "Lack of a buttock" means absent of a buttock or lack of substantially all of a buttock.

"Large buttock" means a buttock which is at least 10% larger (in width, length or prominence, i.e. depth) as compared to the size of the average buttock of persons the same or similar size and weight as the patient.

"Local administration" or "locally administering" means administration (i.e. by injection, implantation or topical application) by a non-systemic route (such as by a subcutaneous, intramuscular, subdermal, intradermal or transdermal route, whereby insignificant amounts of the pharmaceutical agent appear systemically) of a pharmaceutical agent to or to the vicinity of a target dermal or subdermal location (such as to a muscle) of a patient.

"Prominent buttock" means a buttock that has a shape that noticeably protrudes outward compared to the average buttock of other persons of the same or similar size and weight of the patient.

"Square buttock" means that buttock when viewed directly from the rear has a decreased overall curvature of the outline of the buttock as compared to the average buttock of other persons of the same or similar size and weight as the patient.

"Therapeutically effective amount" means the level, amount or concentration of an agent (i.e. an active pharmaceutical ingredient, such as a *botulinum* toxin) needed to treat a disease, disorder or condition without causing significant negative or adverse side effects to the treated tissue.

"Treat", "treating", or "treatment" means an alleviation or a reduction (which includes some reduction, a significant reduction a near total reduction, and a total reduction), resolution or prevention (temporarily or permanently) of an disease, disorder or condition, such as a buttock deformity, so as to achieve a desired therapeutic or cosmetic result, such as by healing of injured or damaged tissue, or by altering, changing, enhancing, improving, ameliorating and/or beautifying an existing or perceived disease, disorder or condition. A treatment effect, such as an alleviating effect from administration of a *botulinum* neurotoxin may not appear clinically for between 1 to 7 days after administration of the *botulinum* neurotoxin to a patient.

"Trauma" means an injury, disease, malady or complication including trauma due to a medical procedure, such as surgery.

"Uneven buttock crease and fold" means the crease and fold of one side of the buttock is not aligned with the crease and fold of the other side of the same buttock.

A method within the scope of the present invention for treating a buttock deformity can have the step of local administration of a Clostridial neurotoxin (such as a *botulinum* toxin) into or to a buttock of a patient, thereby treating the buttock deformity.

The buttock musculature have functions in stability and gait. *Botulinum* toxin is known to have a relaxation effect on muscle and according to the present invention can be used to treat a buttock deformity, through its affect on buttock musculature. Inhibition of acetylcholine release by buttock motor neurons can result in relaxation of the innervated muscle and thereby achieving a symmetrical shape buttock upon injecting the affected muscles. Additionally, according to my invention buttock folds or wrinkles can also be treated with a *botulinum* toxin. Injection of a therapeutic amount of a selected serotype of a *botulinum* toxin can enhance gait and symmetry. In addition to these subcutaneous and intramuscular injections, buttock deformities that cause dysfunction around the sacroiliac joint can be treated by an intra-articular injection of a *botulinum* toxin into the sacroiliac joint to thereby relieve pain and improve gait.

The *botulinum* neurotoxin can be locally administered in an amount of between about $10^{-3}$ units/kg of patient weight and about 35 units/kg of patient weight. Preferably, the neurotoxin is locally administered in an amount of between about $10^{-2}$ U/kg and about 25 U/kg of patient weight. More preferably, the neurotoxin is administered in an amount of between about $10^{-1}$ U/kg and about 15 U/kg. In a particularly preferred method within the scope of the present invention, the neurotoxin is locally administered in an amount of between about 1 U/kg and about 10 U/kg. In a clinical setting it can be advantageous to inject from 1 U to 3000 U of a neurotoxin, such as *botulinum* toxin type A or B, to a buttock by topical application or by subdermal administration, to effectively treat the buttock deformity.

An embodiment of the present invention is a method for treating a buttock deformity, the method comprising the step of administering a *botulinum* toxin to a buttock of a patient, thereby treating the buttock deformity. Preferably, the *botulinum* toxin is selected from the group consisting of *botulinum* toxin types A, B, C, D, E, F and G and more preferably, the *botulinum* toxin is a *botulinum* toxin type A. The *botulinum* toxin is administered intramuscularly, into a gluteal muscle, in an amount of between about 1 unit and about 3,000 units, wherein the gluteal muscle is selected from the group consisting of a gluteus maximus, gluteus medius and gluteus minimus.

The buttock deformity can be a contour deformity, wherein the contour deformity is selected from a group consisting of large buttock, prominent buttock, deficient buttock, flat buttock, lack of a buttock, uneven buttock crease and fold, depressions in the buttock, square buttock shapes, asymmetric ptosis of the buttock and irregularly shaped buttock.

A detailed embodiment of the present invention is a method of treating a buttock deformity, the method comprising the step of locally administering a therapeutically effective amount of a *botulinum* toxin to a buttock deformity of the patient, thereby treating a buttock by removing or reducing the occurrence of the buttock deformity, wherein the treatment of the buttock deformity results in improved gait or enhanced symmetry.

Another embodiment of the present invention is a method for treating a buttock deformity, the method comprising the steps of (a) a buttock modification exercise in conjunction with administering a *botulinum* toxin to a buttock and (b) administering the *botulinum* toxin to a buttock, thereby treating the buttock deformity. Preferably, the *botulinum* toxin is selected from the group consisting of *botulinum* toxin types A, B, C, D, E, F and G and more preferably, the *botulinum* toxin is a *botulinum* toxin type A and is administered in an amount of between about 1 unit and about 3,000 units.

A detailed embodiment of the present invention is a method for treating a buttock deformity, the method comprising the steps of (a) a buttock modification exercise in conjunction with administering a *botulinum* toxin and (b) administering between 1 and about 3,000 units of *botulinum* toxin type A to a buttock, thereby treating the buttock deformity.

A third embodiment of the present invention is a method for treating a buttock deformity, the method comprising the steps of (a) using a foot supporting device in conjunction with administration of a *botulinum* toxin and (b) administering a *botulinum* toxin into a buttock, thereby treating the buttock deformity. Preferably, the *botulinum* toxin is selected from the group consisting of *botulinum* toxin types A, B, C, D, E, F and G and more preferably, the *botulinum* toxin is a *botulinum* toxin type A and is administered in an amount of between about 1 unit and about 3,000 units.

A detailed embodiment of the present invention is a method for treating a buttock deformity, the method comprising the steps of (a) using a foot supporting device in conjunction with administering a *botulinum* toxin and (b) administering between 1 and about 3,000 units of *botulinum* toxin type A to a buttock, thereby treating the buttock deformity.

A fourth embodiment of the present invention is a method for treating an underdeveloped gluteal muscle, the method comprising the step of administering a *botulinum* toxin underneath a buttock fold, thereby treating the underdeveloped gluteal muscle. Preferably, the *botulinum* toxin is selected from the group consisting of *botulinum* toxin types A, B, C, D, E, F and G and more preferably, the *botulinum* toxin is a *botulinum* toxin type A and is administered in an amount of between about 1 unit and about 3,000 units.

A detailed embodiment of the present invention is a method for treating an underdeveloped gluteal muscle, the method comprising the steps of administering between 1 and about 3,000 units of *botulinum* toxin type A underneath a buttock fold, thereby treating the underdeveloped gluteal muscle.

A fifth embodiment of the present invention is a method for treating an arthrogenic inhibition of a gluteus maximus, the method comprising the steps of (a) administering a *botulinum* toxin into a buttock and (b) administering a *botulinum* toxin into a joint, thereby treating the arthrogenic inhibition. Preferably, the *botulinum* toxin is selected from the group consisting of *botulinum* toxin types A, B, C, D, E, F and G and more preferably, the *botulinum* toxin is a *botulinum* toxin type A and is administered in an amount of between about 1 unit and about 3,000 units. The buttock is a gluteus maximus ipsilateral to the arthrogenic inhibition and/or a gluteus medius contralateral to the arthrogenic inhibition. The joint can be a sacroiliac joint.

A detailed embodiment of the present invention is a method for treating an arthrogenic inhibition of a gluteus maximus, the method comprising the steps of administering between 1 and about 3,000 units of *botulinum* toxin type A to (a) a gluteus maximus ipsilateral to the arthrogenic inhibition, (b) a gluteus medius contralateral to the arthrogenic inhibition, and (c) to a sacroiliac joint, thereby treating the arthrogenic inhibition of the gluteus maximus.

A suitable neurotoxin for use in the practice of the present invention can be made by a Clostridial bacterium, such as *Clostridium botulinum, Clostridium butyricum* or *Clostridium beratti*. The neurotoxin use can be a modified neurotoxin, that is, a neurotoxin has had at least one of its amino acids deleted, modified or replaced, as compared to a native neurotoxin. Additionally, the neurotoxin can be recombinantly made produced neurotoxin or a derivative or fragment of a recombinant made neurotoxin. The neurotoxin can be a *botulinum* toxin, such as one of the *botulinum* toxin serotypes A, B, $C_1$, D, E, F or G. A preferred *botulinum* toxin to use in the practice of the present invention is *botulinum* toxin type A.

A method according to my invention can be carried out by administration of a Clostridial toxin to a patient with, or who is predisposed to developing, a buttock deformity. The Clostridial toxin used is preferably a *botulinum* toxin (as either a complex or as a pure [i.e. about 150 kDa molecule], such as a *botulinum* neurotoxin A, B, C1, D, E, F or G. Administration of the Clostridial toxin can be by a transdermal route (i.e. by application of a Clostridial toxin in a cream, patch or lotion vehicle), subdermal route (i.e. subcutaneous or intramuscular) or intradermal route of administration.

The Clostridial neurotoxin is administered in a therapeutically effective amount to alleviate a symptom of a buttock deformity. A suitable Clostridial neurotoxin may be a neurotoxin made by a bacterium, for example, the neurotoxin may be made from a *Clostridium botulinum, Clostridium butyricum,* or *Clostridium beratti.* In certain embodiments of the invention, the buttock deformity can be treated by injecting a *botulinum* toxin intramuscularly. The *botulinum* toxin can be a *botulinum* toxin type A, type B, type C1, type D, type E, type F, or type G. The buttock deformity alleviating effects of the *botulinum* toxin may persist for between about 2 weeks (i.e. upon administration of a short acting *botulinum* toxin, such as a *botulinum* toxin type E or F) and 5 years (i.e. upon implantation of a controlled release *botulinum* toxin implant). The *botulinum* neurotoxin can be a recombinantly made *botulinum* neurotoxins, such as *botulinum* toxins produced by an *E. coli* bacterium. In addition or alternatively, the *botulinum* neurotoxin can be a modified neurotoxin, that is a *botulinum* neurotoxin which has at least one of its amino acids deleted, modified or replaced, as compared to a native or the modified *botulinum* neurotoxin can be a recombinant produced *botulinum* neurotoxin or a derivative or fragment thereof.

DESCRIPTION

The present invention is based upon the discovery that a buttock deformity can be treated by local administration of a therapeutically effective amount of a Clostridial neurotoxin, such as a *botulinum* neurotoxin. The *botulinum* neurotoxin (such as a *botulinum* neurotoxin serotype A, B, $C_1$ D, E, F or G) can be administered by topical application, subdermal injection or intramuscular injection into a buttock of a patient.

My invention includes methods for treating at least the following types of buttock deformities; asymmetric buttock, large buttock, prominent buttock, irregular buttock, deficient buttock, flat buttock, uneven buttock, depressions in the buttock, and square buttock. A *botulinum* toxin can be applied in an effective therapeutic amount by applying about one unit of a *botulinum* toxin type A/cm2 of the affected area. Methods to apply the *botulinum* toxin include but are not limited to subcutaneous, intradermal, intramuscular, topical, and via slow or extended release implants.

Thus, my invention includes use of a *botulinum* toxin to treat a buttock deformity by causing it to become flaccid and/or to relieve the pain and inflammation that can accompany a buttock deformity.

The amount of the Clostridial toxin administered according to a method within the scope of the disclosed invention can vary according to the particular characteristics of the buttock deformity being treated, including its severity and other various patient variables including size, weight, age, and responsiveness to therapy. To guide the practitioner, typically, no less than about 5 units and no more than about 500 units of a *botulinum* toxin type A (such as BOTOX®) is administered per injection site (i.e. to each buttock deformity location injected), per patent treatment session. For a *botulinum* toxin type A such as DYSPORT®, preferably no less than about 10 units and no more about 2000 units of the *botulinum* toxin type A are administered per administration or injection site, per patent treatment session. For a *botulinum* toxin type B such as MYOBLOC®, preferably no less than about 200 units and no more than about 25000 units of the *botulinum* toxin type B are administered per administer or injection site, per patient treatment session. Less than about 5, 10 or 200 units (of BOTOX®, DYSPORT® and MYOBLOC® respectively) can fail to achieve a desired therapeutic effect, while more than about 500, 2000 or 25000 units (of BOTOX®, DYSPORT® and MYOBLOC® respectively) can result in clinically observable and undesired muscle hypotonicity, weakness and/or paralysis.

More preferably: for BOTOX® no less than about 10 units and no more about 400 units of a *botulinum* toxin type A; for DYSPORT® no less than about 30 units and no more than about 1600 units, and; for MYOBLOC®, no less than about 250 units and no more than about 20000 units are, respectively, administered per injection site, per patient treatment session.

Most preferably: for BOTOX® no less than about 20 units and no more than about 300 units of a *botulinum* toxin type A; for DYSPORT® no less than about 60 units and no more than about 1200 units, and; for MYOBLOC®, no less than about 1000 units and no more than about 15000 units are, respectively, administered per injection site, per patient treatment session. It is important to note that there can be multiple injection sites (i.e. a pattern of injections) for each patient treatment session.

Although examples of routes of administration and dosages are provided, the appropriate route of administration and dosage are generally determined on a case by case basis by the attending physician. Such determinations are routine to one of ordinary skill in the art (see for example, *Harrison's Principles of Internal Medicine* (1998), edited by Anthony Fauci et al., 14th edition, published by McGraw Hill). For example, the route and dosage for administration of a Clostridial neurotoxin according to the present disclosed invention can be selected based upon criteria such as the solubility characteristics of the neurotoxin chosen as well as the intensity and scope of a buttock deformity.

The present invention is based on the discovery that local administration of a Clostridial toxin can provide significant and long lasting relief from a buttock deformity. A Clostridial toxin used in accordance with the invention disclosed herein can inhibit transmission of chemical or electrical signals between select neuronal groups that are involved in generation of a buttock deformity. The Clostridial toxins preferably are not cytotoxic to the cells that are exposed to the Clostridial toxin. The Clostridial toxin can inhibit neurotransmission by reducing or preventing exocytosis of neurotransmitter from the neurons exposed to the Clostridial toxin. Alternatively, the applied Clostridial toxin can reduce neurotransmission by inhibiting the generation of action potentials of the neurons exposed to the toxin. The buttock deformity alleviation effect provided by the Clostridial toxin can persist for a relatively long period of time, for example, for more than two months (or for 2-4 weeks upon use of a *botulinum* toxin type E or F), and potentially for several years.

Examples of Clostridial toxins within the scope of the present invention include neurotoxins made by *Clostridium*

*botulinum*, *Clostridium butyricum* and *Clostridium beratti* species. In addition, the *botulinum* toxins used in the methods of the invention can be a *botulinum* neurotoxin selected from a group of *botulinum* toxin types A, B, $C_1$, D, E, F, and G. In one embodiment of the invention, the *botulinum* neurotoxin administered to the patient is *botulinum* toxin type A. *Botulinum* toxin type A is desirable due to its high potency in humans, ready availability, and known use for the treatment of skeletal and smooth muscle disorders when locally administered by intramuscular injection. The present invention also includes the use of (a) Clostridial neurotoxins obtained or processed by bacterial culturing, toxin extraction, concentration, preservation, freeze drying, and/or reconstitution; and/or (b) modified or recombinant neurotoxins, that is neurotoxins that have had one or more amino acids or amino acid sequences deliberately deleted, modified or replaced by known chemical/biochemical amino acid modification procedures or by use of known host cell/recombinant vector recombinant technologies, as well as derivatives or fragments of neurotoxins so made. These neurotoxin variants retain the ability to inhibit neurotransmission between or among neurons, and some of these variants may provide increased durations of inhibitory effects as compared to native neurotoxins, or may provide enhanced binding specificity to the neurons exposed to the neurotoxins. These neurotoxin variants may be selected by screening the variants using conventional assays to identify neurotoxins that have the desired physiological effects of inhibiting neurotransmission.

*Botulinum* toxins for use according to the present invention can be stored in lyophilized, vacuum dried form in containers under vacuum pressure or as stable liquids. Prior to lyophilization the *botulinum* toxin can be combined with pharmaceutically acceptable excipients, stabilizers and/or carriers, such as albumin. The lyophilized material can be reconstituted with saline or water to create a solution or composition containing the *botulinum* toxin to be administered to the patient.

Although the composition may only contain a single type of neurotoxin, such as *botulinum* toxin type A, as the active ingredient to suppress neurotransmission, other therapeutic compositions may include two or more types of neurotoxins, which may provide enhanced therapeutic treatment of a buttock deformity. For example, a composition administered to a patient may include *botulinum* toxin type A and *botulinum* toxin type B. Administering a single composition containing two different neurotoxins can permit the effective concentration of each of the neurotoxins to be lower than if a single neurotoxin is administered to the patient while still achieving the desired therapeutic effects. The composition administered to the patient may also contain other pharmaceutically active ingredients, such as, protein receptor or ion channel modulators, in combination with the neurotoxin or neurotoxins. These modulators may contribute to the reduction in neurotransmission between the various neurons. For example, a composition may contain gamma aminobutyric acid (GABA) type A receptor modulators that enhance the inhibitory effects mediated by the GABAA receptor. The GABAA receptor inhibits neuronal activity by effectively shunting current flow across the cell membrane. GABAA receptor modulators may enhance the inhibitory effects of the GABAA receptor and reduce electrical or chemical signal transmission from the neurons. Examples of GABAA receptor modulators include benzodiazepines, such as diazepam, oxaxepam, lorazepam, prazepam, alprazolam, halazeapam, chordiazepoxide, and chlorazepate. Compositions may also contain glutamate receptor modulators that decrease the excitatory effects mediated by glutamate receptors. Examples of glutamate receptor modulators include agents that inhibit current flux through AMPA, NMDA, and/or kainate types of glutamate receptors. The compositions may also include agents that modulate dopamine receptors, such as antipsychotics, norepinephrine receptors, and/or serotonin receptors. The compositions may also include agents that affect ion flux through voltage gated calcium channels, potassium channels, and/or sodium channels. Thus, the compositions used to treat a buttock deformity can include one or more neurotoxins, such as *botulinum* toxins, in addition to ion channel receptor modulators that may reduce neurotransmission.

The neurotoxin may be administered by any suitable method as determined by the attending physician. The methods of administration permit the neurotoxin to be administered locally to a selected target tissue. Methods of administration include injection of a solution or composition containing the neurotoxin, as described above, and include implantation of a controlled release system that controllably releases the neurotoxin to the target tissue. Such controlled release systems reduce the need for repeat injections. Diffusion of biological activity of a *botulinum* toxin within a tissue appears to be a function of dose and can be graduated. Jankovic J., et al *Therapy With Botulinum Toxin*, Marcel Dekker, Inc., (1994), page 150. Thus, diffusion of *botulinum* toxin can be controlled to reduce potentially undesirable side effects that may affect the patient's cognitive abilities. For example, the neurotoxin can be administered so that the neurotoxin primarily affects neural systems believed to be involved in the generation of a buttock deformity.

A polyanhydride polymer, Gliadel® (Stolle R & D, Inc., Cincinnati, Ohio) a copolymer of poly-carboxyphenoxypropane and sebacic acid in a ratio of 20:80 has been used to make implants, and has been intracranially implanted to treat malignant gliomas. Polymer and BCNU can be co-dissolved in methylene chloride and spray-dried into microspheres. The microspheres can then be pressed into discs 1.4 cm in diameter and 1.0 mm thick by compression molding, packaged in aluminum foil pouches under nitrogen atmosphere and sterilized by 2.2 megaRads of gamma irradiation. The polymer permits release of carmustine over a 2-3 week period, although it can take more than a year for the polymer to be largely degraded. Brem, H., et al, *Placebo-Controlled Trial of Safety and Efficacy of Intraoperative Controlled Delivery by Biodegradable Polymers of Chemotherapy for Recurrent Gliomas*, Lancet 345;1008-1012:1995.

Implants useful in practicing the methods disclosed herein may be prepared by mixing a desired amount of a stabilized neurotoxin (such as non-reconstituted BOTOX®) into a solution of a suitable polymer dissolved in methylene chloride. The solution may be prepared at room temperature. The solution can then be transferred to a Petri dish and the methylene chloride evaporated in a vacuum desiccator. Depending upon the implant size desired and hence the amount of incorporated neurotoxin, a suitable amount of the dried neurotoxin incorporating implant is compressed at about 8000 p.s.i. for 5 seconds or at 3000 p.s.i. for 17 seconds in a mold to form implant discs encapsulating the neurotoxin. See e.g. Fung L. K. et al., *Pharmacokinetics of Interstitial Delivery of Carmustine 4-Hydroperoxycyclophosphamide and Paclitaxel From a Biodegradable Polymer Implant in the Monkey Brain*, Cancer Research 58; 672-684:1998.

Local administration of a Clostridial toxin, such as a *botulinum* toxin, can provide a high, local therapeutic level of the toxin. A controlled release polymer capable of long term, local delivery of a Clostridial toxin to a target buttock deformity location permits effective dosing of the target tissue. A suitable implant, as set forth in U.S. Pat. No. 6,306,423 entitled "Neurotoxin Implant", allows the direct introduction of a chemotherapeutic agent to a target tissue via a controlled release polymer. The implant polymers used are preferably hydrophobic so as to protect the polymer incorporated neurotoxin from water induced decomposition until the toxin is released into the target tissue environment.

Local administration of a *botulinum* toxin, according to the present invention, by injection or implant to a target tissue provides a superior alternative to systemic administration of pharmaceuticals to patients to alleviate a buttock deformity.

The amount of a Clostridial toxin selected for local administration to a target tissue according to the present disclosed invention can be varied based upon criteria such as the severity of the buttock deformity being treated, solubility characteristics of the neurotoxin toxin chosen as well as the age, sex, weight and health of the patient. For example, the extent of the area of muscle influenced is believed to be proportional to the volume of neurotoxin injected, while the quantity of the buttock deformity suppressant effect is, for most dose ranges, believed to be proportional to the concentration of a Clostridial toxin administered. Methods for determining the appropriate route of administration and dosage are generally determined on a case by case basis by the attending physician. Such determinations are routine to one of ordinary skill in the art (see for example, *Harrison's Principles of Internal Medicine* (1998), edited by Anthony Fauci et al., 14th edition, published by McGraw Hill).

Significantly, a method within the scope of the present invention can provide improved patient function. "Improved patient function" can be defined as an improvement measured by factors such as a reduced pain, reduced time spent in bed, increased ambulation, healthier attitude, more varied lifestyle and/or healing permitted by normal muscle tone. Improved patient function is synonymous with an improved quality of life (QOL). QOL can be assessed using, for example, the known SF-12 or SF-36 health survey scoring procedures. SF-36 assesses a patient's physical and mental health in the eight domains of physical functioning, role limitations due to physical problems, social functioning, bodily pain, general mental health, role limitations due to emotional problems, vitality and general health perceptions. Scores obtained can be compared to published values available for various general and patient populations.

EXAMPLES

The following non-limiting examples provide those of ordinary skill in the art with specific preferred methods to treat conditions within the scope of the present invention and are not intended to limit the scope of the invention. In the following examples various modes of non-systemic administration of a Clostridial neurotoxin can be carried out. For example, by topical application (cream or transdermal patch), subcutaneous injection, intramuscular injection or by implantation of a controlled release implant.

Example 1

Use of *Botulinum* Toxin to Treat a Buttock Deformity Due to a Limb-Length Discrepancy A 21 year old female can have been followed in a podiatry clinic since age 13 for a functional limb length discrepancy that can be related to abnormal pronation of the foot. Upon examination, it can be determined that the patient has excessive pronation in longer limb and supination in shorter limb. That the right arm, shorter (affected side) than the left, hangs away from the body, while the left arm (long side) can rest against the body. The patient can have difference in levels of malleolar, knee and hip positions; uneven shoulder height, and her gluteal fold lower on short side and iliac crests can be uneven, with the appearance of dimpling of the left gluteus maximus. In addition to the functional issues, the patient can also have significant concerns regarding her misshapen gluteal appearance.

Initial treatment can include muscle strengthening and stretching exercises. However, no or insufficient changes may be noted in the pronation or pain generated by the abnormal posturing. The patient can have been referred to a podiatrist who can fit her with an orthotic for six months, as a functional orthotic device in an attempt to correct the pronatory motion, but the results may have been unsatisfactory. Without wanting to undergo an invasive surgical procedure, the patient can agree to a course of *botulinum* toxin type A in an effort to correct the asymmetry of the gluteal folds and the apparent limb-length inequality. The gluteus maximus on the right side, the affected limb, and of the gluteus medius, on the contralateral side, can be injected intramuscularly with 100 U and 75 U respectively of BOTOX®. Alternately about 300-400 units of a *botulinum* toxin type A such as Dysport® or about 5000 units of a *botulinum* toxin type B such as MyoBloc® can be used. Upon follow-up one month later, corrections to the patient's posture and asymmetry can be noted. Upon further examination, the irregularity of gluteal asymmetry and dimpling can have almost totally resolved. The patient can report one month later an almost symmetric appearance of her gluteal muscles, and a more active social life.

Example 2

Use of *Botulinum* Toxin to Treat a Buttock Deformity Due to Underdeveloped Gluteal Muscles A 31 year old male weightlifter can request buttock sculpting to augment his underdeveloped gluteal muscles to give him a more balanced look to improve overall body aesthetics which is important to him as the patient competes in body-building competitions. Since the patient can have less actual body fat percentage than normal to undergo liposuction sculpting, the patient can agree to a course of neurosculpting therapy using a *botulinum* toxin type A (BOTOX®). The clinician can inject subcutaneously 75 units just under the buttock folds bilaterally using 100 U per side (or alternately about 300-400 units of a *botulinum* toxin type A such as Dysport® or about 5000 units of a *botulinum* toxin type B such as MyoBloc®). Upon follow up a symmetric appearance with a prominent fold (relaxation of the gluteal muscles can result in defined rounded with slight downward direction) can be noted. The patient can be very pleased with the results, reporting no adverse events and that he was the first place contestant in a major bodybuilding competition a one month later.

Example 3

Use of *Botulinum* Toxin to Treat a Buttock Deformity Due to Spasms of the iliacus and Arthrogenic Inhibition of the Gluteus Maximus A 48 year old male can be seen in an orthopedics clinic reporting painful spasms of the iliacus, and of sacroiliac joint.

Upon examination, there can be revealed an arthrogenic inhibition of the gluteus maximus on the side of the blocked joint and of the gluteus medius on the contralateral side, causing an asymmetric of his buttocks. Since this is often a result of a typical pattern of changes in muscle activation a course of a *botulinum* toxin type A (BOTOX®) can be decided upon and 75 U can be injected into the affected gluteus maximus, 50 U into the gluteus medius, and 100 U injected intra-articularly into the sacroiliac joint space. Alternately about 300-400 units of a *botulinum* toxin type A such as DYSPORT® or about 5000 units of a *botulinum* toxin type B such as MYOBLOC® can be used. Upon follow-up 6 weeks later the patient can report significant reductions in pain and spasm, and upon examination symmetrical buttock shape can be noted.

Example 4

Use of *Botulinum* Toxin to Treat a Buttock Deformity Manifested as an Uneven Buttock due to a Genetic Birth Defect A 22 year old female can be affected by a genetic birth defect that can cause an uneven buttock crease and fold, depressions in the left buttock and result in an irregularly shaped buttock. The patient can have visited her aesthetic surgeon as she wishes to enhance her gluteal contour, resulting in a more aesthetic symmetric appearance. Since the patient can have recently undergone liposuction for the abdominal area, surgery (placement of implants) is not recommended, and therefore, the clinician can recommend a non-invasive trial of a *botulinum* toxin type A (BOTOX®) to sculpt the affected buttock region. 75 U can be injected subcutaneously into the gluteus maximus and 50 U into the gluteus minimus, both on the left side. An additional 50 U can be injected following small creases and some finer wrinkles. Alternately about 300-400 units of a *botulinum* toxin type A such as DYSPORT® or about 5000 units of a *botulinum* toxin type B such as MYOBLOC® can be used. Upon follow up examination 1 month later, the asymmetry of the gluteal contour can be 75-85% symmetric. Both the patient and clinician can be pleased with the minimally invasive procedure. The patient can return 3 months following the first treatment for a 2$^{nd}$ treatment where there can be an almost 100% improvement over her original baseline appearance.

In each of the examples above a *botulinum* toxin type B, C, D, E, F or G can be substituted for the *botulinum* toxin type A used above. The specific amount of a *botulinum* toxin (such as BOTOX®) administered depends upon a variety of factors to be weighed and considered within the discretion of the attending physician and in each of the examples insignificant amounts of *botulinum* toxin enter appear systemically with no significant side effects.

A method for treating a buttock deformity according to the invention disclosed herein has many benefits and advantages, including the following:

1. the symptoms of a buttock deformity can be dramatically reduced or eliminated.

2. the symptoms of a buttock deformity can be reduced or eliminated for at least about two weeks to about six months per injection of neurotoxin and for from about one year to about five years upon use of a controlled release neurotoxin implant.

3. the injected or implanted Clostridial neurotoxin shows little or no tendency to diffuse or to be transported away from the intramuscular (or intradermal or subdermal) injection or implantation site.

4. few or no significant undesirable side effects occur from intramuscular (or intradermal or subdermal) injection or implantation of the Clostridial neurotoxin.

5. the present methods can result in the desirable side effects of greater patient mobility, a more positive attitude and an improved quality of life.

Although the present invention has been described in detail with regard to certain preferred methods, other embodiments, versions, and modifications within the scope of the present invention are possible. For example, a wide variety of neurotoxins can be effectively used in the methods of the present invention. Additionally, the present invention includes local administration methods to alleviate a buttock deformity wherein two or more neurotoxins, such as two or more *botulinum* toxins, are administered concurrently or consecutively. For example, *botulinum* toxin type A can be administered until a loss of clinical response or neutralizing antibodies develop, followed by administration of *botulinum* toxin type B. Alternately, a combination of any two or more of the *botulinum* serotypes A-G can be locally administered to control the onset and duration of the desired therapeutic result. Furthermore, non-neurotoxin compounds can be administered prior to, concurrently with or subsequent to administration of the neurotoxin to proved adjunct effect such as enhanced or a more rapid onset of denervation before the neurotoxin, such as a *botulinum* toxin, begins to exert its therapeutic effect.

A *botulinum* toxin can be administered by itself or in combination of one or more of the other *botulinum* toxin serotypes. The *botulinum* toxin can be a recombinantly made or a hybrid *botulinum* toxin.

My invention also includes within its scope the use of a neurotoxin, such as a *botulinum* toxin, in the preparation of a medicament for the treatment of a buttock deformity, by local administration of a *botulinum* neurotoxin.

All references, articles, patents, applications and publications set forth above are incorporated herein by reference in their entireties.

Accordingly, the spirit and scope of the following claims should not be limited to the descriptions of the preferred embodiments set forth above.

I claim:

1. A method for treating a buttock deformity, the method comprising administering about 200 to about 25,000 units of a *botulinum* toxin type B in pure or hybrid form or as a complex, to a buttock of a patient having a buttock deformity, thereby reducing the buttock deformity.

2. The method of claim 1, wherein the buttock deformity is a contour deformity.

3. The method of claim 2, wherein the contour deformity is selected from the group consisting of large buttock, prominent buttock, deficient buttock, flat buttock, lack of a buttock, uneven buttock crease and fold, depressions in the buttock, square buttock shapes, asymmetric ptosis of the buttock and irregularly shaped buttock.

4. The method of claim 1 further comprising the step of using a foot supporting device in conjunction with administering the *botulinum* toxin to the patient.

5. A method for treating a buttock deformity, the method comprising administering about 1000 to about 15,000 units of a *botulinum* toxin type B in pure or hybrid form or as a complex to a buttock of a patient having a buttock deformity, thereby reducing the buttock deformity.

6. The method of claim 5, wherein the about 1000 to about 15,000 units of a *botulinum* toxin type B is administered at multiple injection sites per patient treatment session.

7. The method of claim 5, wherein administration to the buttock is subcutaneous, intramuscular, subdermal, intradermal or transdermal.

8. The method of claim 5, wherein the buttock deformity is a contour deformity.

9. The method of claim 8, wherein the contour deformity is selected from the group consisting of large buttock, prominent buttock, deficient buttock, flat buttock, lack of a buttock, uneven buttock crease and fold, depressions in the buttock, square buttock shapes, asymmetric ptosis of the buttock and irregularly shaped buttock.

* * * * *

UNITED STATES PATENT AND TRADEMARK OFFICE
CERTIFICATE OF CORRECTION

PATENT NO. : 7,438,921 B2  Page 1 of 1
APPLICATION NO. : 11/622420
DATED : October 21, 2008
INVENTOR(S) : Eric R. First It is certified that error appears in the above-identified patent and that said Letters Patent is hereby corrected as shown below:

Title page, Item (56), under "Other Publications", in column 2, line 17, delete "fo" and insert -- of --, therefor.

On page 2, Title page, Item (56), under "Other Publications", in column 2, line 40, delete "piripormis" and insert -- piriformis --, therefor.

In column 1, line 8, delete "entirely." and insert -- entirety. --, therefor.

In column 2-3, line 67, delete "Botulinum-Toxin" and insert -- Botulinum Toxin --, therefor.

In column 6, line 67, delete "supercilli" and insert -- supercilii --, therefor.

In column 9, line 3, delete "Berg" and insert -- Belg --, therefor.

In column 9, line 30, delete "gangliocide" and insert -- ganglioside --, therefor.

In column 9, line 67, delete "norepinephine." and insert -- norepinephrine. --, therefor.

In column 12, line 18, after "patient" insert -- . --.

Signed and Sealed this

Sixth Day of January, 2009

JON W. DUDAS
*Director of the United States Patent and Trademark Office*